United States Patent [19]

Bargigia et al.

[11] Patent Number: 4,806,662

[45] Date of Patent: Feb. 21, 1989

[54] FLUIDS HAVING AN OXETANE STRUCTURE AND IMPROVED CHARACTERISTICS FOR SPECIAL APPLICATIONS

[75] Inventors: Gianangelo Bargigia; Gerardo Caporiccio; Claudio Tonelli; Luciano Flabbi, all of Milan, Italy

[73] Assignee: Ausimont S.p.A., Milan, Italy

[21] Appl. No.: 828,682

[22] Filed: Feb. 12, 1986

[30] Foreign Application Priority Data

Feb. 13, 1985 [IT] Italy ............................... 19496 A/85

[51] Int. Cl.$^4$ ........................................... C07D 305/08
[52] U.S. Cl. ................................................ 549/511
[58] Field of Search ......................................... 549/511

[56] References Cited

U.S. PATENT DOCUMENTS

| | | | |
|---|---|---|---|
| 2,594,272 | 4/1952 | Kauck et al. | 549/511 |
| 2,995,571 | 8/1961 | Harris | 549/511 |
| 2,995,572 | 8/1961 | Harris | 549/511 |
| 3,114,778 | 12/1963 | Fritz et al. | 568/674 |
| 3,125,581 | 3/1964 | Coffman et al. | 549/511 |
| 3,180,895 | 4/1965 | Harris et al. | 568/685 |
| 3,291,843 | 12/1966 | Fritz et al. | 568/686 |
| 3,847,978 | 11/1974 | Sianesi et al. | |
| 4,709,060 | 11/1987 | Ohsaka et al. | 549/511 |

FOREIGN PATENT DOCUMENTS

| | | | |
|---|---|---|---|
| 150055 | 7/1985 | European Pat. Off. | 549/511 |
| 1033919 | 6/1966 | United Kingdom . | |
| 1231966 | 5/1971 | United Kingdom | 549/511 |

OTHER PUBLICATIONS

Chemical Abstracts 101:90425y.
G. Bargigia et al., Journal of Fluorine Chemistry, vol. 36 (1987), pp. 449–459.
R. E. Banks, Preparation, Properties, and Industrial Applications of Organofluorine Compounds, John Wiley & Sons (1982), pp. 28–29;256–257;289–290.

*Primary Examiner*—Richard L. Raymond
*Assistant Examiner*—Mark W. Russell
*Attorney, Agent, or Firm*—Stevens, Davis, Miller & Mosher

[57] ABSTRACT

Oxetane-structure fluids of well-defined composition and free from not completely fluorinated compounds, characterized in that they have at least a perfluoroether chain bound to an oxetane ring, having improved characteristics for special applications, being liquid up to temperatures of at least $-70°$ C., having boiling temperatures in the range of from 50° to 270° C. or higher, and a very high range between the boiling temperature and the pour point.

2 Claims, No Drawings

FLUIDS HAVING AN OXETANE STRUCTURE AND IMPROVED CHARACTERISTICS FOR SPECIAL APPLICATIONS

THE PRESENT INVENTION

This invention relates to new oxetanes having improved characteristics which render them suitable for particular applications in advanced industrial fields.

In particular, this invention relates to new fluids of well-defined compositions of the class of the oxetanes, which are liquid up to temperatures of at least −70° C., are free from not completely fluorinated compounds, and exhibit boiling temperatures comprised in a very narrow range, with the difference between boiling temperature and pour point being very high. The term "pour point" means the temperature at which the liquid, modifies its physical properties on cooling, i.e. its flowability decreases as the viscosity increases.

A further object of the present invention is that of providing a process for preparing the abovesaid oxetanes which does not require the use of hydrofluoric acid, or elemental fluorine during the synthesis process, thus considerably simplifying the industrial synthesis of the products of the invention.

DESCRIPTION OF THE PRIOR ART

As is known, the available compounds having a high fluorine content are endowed with an exceptional combination of excellent properties which make them suitable for a very great number of utilizations in many industrial fields.

The main properties are chemical inertia, thermal stability, non-inflammability, high electrical resistivity, low surface tension, low water-solubility, consistency with many materials, such as elastomers and plastomers.

The known products are affected, however, by the drawback of not possessing good characteristics for certain special applications in advanced industrial fields.

Compounds obtained by flourination in the presence of $CoF_3$ of cycloaliphatic or aromatic hydrocarbons are known.

A representation example of these compounds is perfluoromethylcyclohexane obtained by reaction of toluene in the presence of $CoF_3$.

The resulting fluids require, for their synthesis, the use of particularly sophisticated equipment which can resist both the fluorine utilized to regenerate $CoF_3$ that undergoes a reduction during the synthesis, and the high temperatures usually necessary for said synthesis. Furthermore, as the reaction proceeds, the substitution of the hydrogen atoms of the hydrocarbon, utilized as a precursor of the perfluorinated compounds to be prepared, becomes more and more difficult, so that a not completely fluorinated fluid is obtained, which contains by-products still having hydrogen atoms.

The presence of these by-products reduces, among other things, the thermal stability as well as the chemical and thermal inertia of the product, thus reducing the application field of these fluorinated fluids.

Furthermore, the methods of separating said not completely fluorinated by-products are very expensive and difficult. However, these fluids, even if thoroughly fluorinated, exhibit boiling temperatures not very high if the pour point is very low.

For example, for a pour point of −70° C., the boiling temperature is at the maximum of the order of 100° C.

The products having a higher boiling temperatures, of the order of 210° C., exhibit the drawback of having too high pour points, of the order of −20° C.

The range from the boiling temperature to the pour point is generally rather high, however the combination of the two values in the same perfluorinated compound renders such products not suited to particular utilizations.

For example, for the thermal shock test hereinafter described, these perfluorinated compounds must be employed in couples because in this application there are required fluids having, at the same time, a high boiling temperature along with a very low pour point.

Perfluorinated compounds with ether or aminic structure obtained by electrofluorination of the corresponding hydrogenated compound in hydrofluoric acid are also known too. A representative example of these compounds is perfluorotributylamine.

Also in such case, expensive synthesis apparatuses are necessary due to the use of anhydrous hydrofluoric acid as a fluorinating agent of the hydrogenated precursors of the product to be prepared.

Furthermore, the resultant fluids are not fully fluorinated, similarly to what has been explained with regard to the perfluorinated fluids described hereinabove.

These compounds exhibit the same drawbacks of the preceding perfluorinated fluids.

There are also known perfluoropolyethers prepared by photo-oxidation of perfluoroolefins, such as $C_2F_4$ and $C_3F_6$. These fluids are utilizable up to very low temperatures, even lower than −70° C., because they remain liquid at such temperature, however, they exhibit the drawback of not having ah defined boiling temperature.

As it is well known, the perfluoropolyethers consist of mixtures of polymers of different molecular weight, wherefore the boiling temperature is not well defined, but varies over a rather wide range. Even by carrying out rectification on the ones usually employed in the industrial practice, it is not possible to obtain perfluoropolyethers having a narrow boiling temperature range beyond a certain limit. Generally, such range is from 30° to 40° C. That renders the perfluoropolyethers not particularly suitable for special applications, such as for example vapor phase soldering or vapor phase curing. In fact the perfluoropolyethers tend, during boiling, to lose the compounds of lower molecular weight, what results in an alteration of the composition of the mixture and, by consequence, of the related boiling point.

This is a drawback, as the boiling temperature must remain, during these applications, as constant as possible in order not to alter the soldering and curing characteristics of the resins, which would lead to products of lower quality.

Furthermore, the perfluoropolyethers are little suitable for being utilized as cooling fluids for electrical devices, as the available mixtures usually have average boiling temperatures higher than the utilization conditions of said devices. In fact, there are no mixtures of perfluoropolyethers having a boiling temperature ranging from 50° to 100° C.

There are also known eyelic perfluorinated compounds of the class of the oxetanes, prepared by addition reaction of a fluorocarbonyl compound with fluoroolefins in the presence of U.V. radiations.

The utilizable fluorocarbonyl compounds have formula RfCOX, in which X=H, F, Rf, and in which Rf=CF$_3$, H(CF$_2$)$_4$, C$_3$F$_7$, ClCF$_2$, C$_2$F$_5$, C$_7$F$_{15}$.

The fluoroolefins have general formula RCF=CFR', wherein R=H, Cl, CF$_3$ and R'=H, F. The resulting oxetanes have general formula

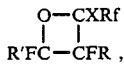

are colorless liquids having a boiling point in a narrow range, but they have the drawbacks of not being liquid at low temperatures, at least up to −70° C.

Examples of oxetanes are described in J. Chem. Soc., Perkin I, 1980, page 2258 in the article "Heterocyclic Polyfluorocompounds, Part. 31. Photochemical Oxetane Formation from Fluoroketones and Perfluoroaldehydes and 1,2-Difluoroethylene" by M. G. Barlow, B. Coles and R. N. Haszeldine.

The fact of having a pour point, or a first order transition point, not very low, renders these compounds unsuitable for the applications mentioned hereinbefore.

DESCRIPTION OF THE INVENTION

The object of this invention is that of providing perfluorinated fluids which are endowed, besides with the abovesaid properties of the perfluorinated compounds of the perfluoropolyethers, also with a wide range between the boiling temperature and the pour point, and with a boiling temperature in the order of 4° C., which make them suitable for the applications described hereinbefore.

Furthermore, the compounds of the invention can have not very high boiling temperatures, of the order of 50° C., or very high temperatures, higher than 270° C., though remaining in the liquid state even to very low temperatures, which renders them suited to other above-mentioned special applications.

The fluids of the invention belong to the class of the perfluoroethers, do not contain, as impurities, not fully fluorinated compounds, and are preparable by synthesis according to a process which avoids the use of hydrofluoric acid or of elemental fluorine.

The perfluoroethers forming the object of the present invention are oxetanes belonging to the following classes of general formula:

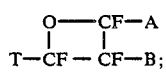 (1)

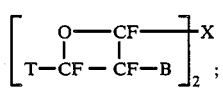 (2)

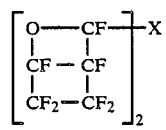 (3)

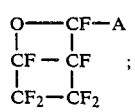 (4)

wherein A=F, or a perfluoroalkyl radical Rf with 1 to 8 carbon atoms, or a group ORf, or a group:

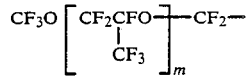

in which m is an integer from 0 to 5 (extremes included), or a group:

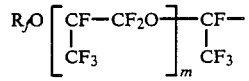

in which
m has the same meaning specified hereinabove and R$_f$ is a perfluoroalkyl with 1 to 8 carbon atoms;
B and T, like or unlike each other, may be:
  F, a perfluoroalkyl radical with 1 to 7 carbon atoms, a group

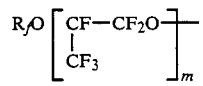

in which m and R$_f$ have the same meaning as specified hereinabove;
X is equal to a group —CF$_2$O—(CF$_2$O)$_p$—(C$_2$F$_4$O)$_q$—CF$_2$— wherein p and q, like or unlike each other, are integers from 0 to 5 (extremes included) and the sum p+q is at least equal to 1, or is a group —(CF$_2$)$_r$— in which r is an integer from 1 to 8; and characterized in that at least one of groups A, B, T in class (1), or B, T, X in class (2), is ≠F and contains one or more ether oxygen atoms; in the classes (3) and (4) the groups X and A are ≠F and are selected from the above-indicated radicals containing one or more ethereal oxygen atoms; furthermore characterized in that when one of radicals B or T is equal to group

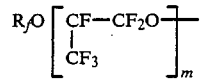

the other is equal to F.
Radicals A, B, T are preferably selected from:

A = CF$_3$—CF$_2$, CF$_3$(CF$_2$)$_6$, CF$_3$CF$_2$CF$_2$O 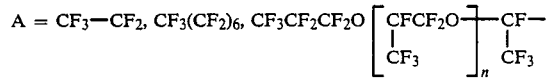

where
n=0, 1, 2, more preferably 0, 1;
B and T, like or unlike each other, are:

F, CF$_3$, CF$_3$(CF$_2$)$_4$, CF$_3$CF$_2$CF$_2$O 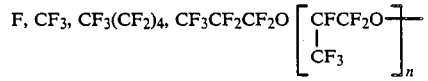

more preferably CF$_3$, and
wherein n has the meaning specified hereinbefore.

The oxetanes of the present invention are generally mixtures of identical products, as regards the empirical formula, but differ from one another as regards the different position of the substituent groups in the oxetane ring, and the various substituents may be in position cis or trans. Furthermore, the presence of quaternary carbon atoms yields optic isomers.

There are listed examples of groups A, B, T, X of the various classes, it being understood that each combination of the various groups is present in the form of mixtures of isomers of position cis and trans, and optic isomers.

The synthesis reaction among the reagents occurs statistically and leads to the formation of all the possible above-listed isomers.

Examples of compounds of class (1) are those in which groups A, B, T are combined as specified hereinbelow:

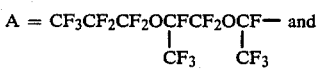

B = F, T = CF$_3$, or B = CF$_3$, T = F;

B = F, T = CF$_3$, or B = CF$_3$, T = F;

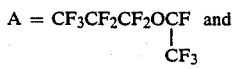

B = F, T = n-C$_5$F$_{11}$, or B = n-C$_5$F$_{11}$, T = F;

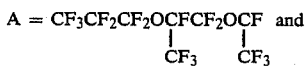

B = F, T = n-C$_3$F$_7$O, or B = n-C$_3$F$_7$O, T = F;

 and

B = F, T = n-C$_3$F$_7$O, or B = n-C$_3$F$_7$O, T = F;

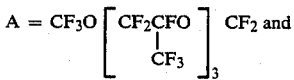

B = F, T = CF$_3$, or B = CF$_3$, T = F.

Examples of compounds of class 2 are the following combinations of X, B, T:
X=CF$_2$OCF$_2$OC$_2$F$_4$OCF$_2$ and
B=F, T=CF$_3$, or
B=CF$_3$, T=F;
X=(CF$_2$)$_4$ and
B=F, T=n—C$_3$F$_7$O, or
B=n—C$_3$F$_7$O, T=F.

Examples of compounds of class 3 are those in which X has the following meaning:
X=CF$_2$OCF$_2$OC$_2$F$_4$OCF$_2$, CF$_2$OC$_2$F$_4$OCF$_2$.

Examples of compounds of class 4 are those in which A has the following meaning:

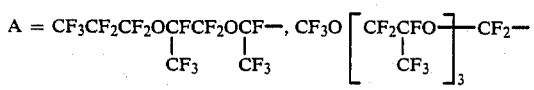

The oxetanes of the invention can be prepared by cycloaddition reaction between a fluoride of a perfluorinated acid and a linear, branched or cyclic perfluoroolefin in which at least one of the reacting compounds contains at least 1 ether oxygen atom. However, it is preferable to employ perfluorinated acids which contain ether oxygen atoms in the chain, as compounds having a perfluoroether structure.

The fluorides of the perfluorinated acids have the following general formula: A—COF, or FOC—X—COF, wherein X and A have the meaning specified hereinabove.

The fluorinated olefins have the general formula: B—CF=CF—T, wherein B, T have the meanings indicated hereinabove, or have cyclic the structure:

Other oxetanes suitable for the applications of the present invention can be obtained also by reacting a perfluorinated diolefin with a fluoride of a perfluorinated acid.

The reaction is preferably conducted under the action of ultraviolet radiation, employing molar ratios between the fluoride of the perfluorinated acid and the perfluoro-olefin ranging from 1:0.9 to 1:15, preferably from 1:2 to 1:8.

The reactor consists of a photochemical quartz unit, and is characterized by an U.V. lamp in the central hollow space, so that all the radiation may pass through the reacting mixture, and it is furthermore characterized by a coolant circulation jacket in order to prevent superheating of the reacting mixture.

The reaction temperature may vary over a wide range, generally from −90° C. to +120° C.

It can be operated both at ambient pressure and at lower or higher pressures, in particular it is operated in the range of from 1 to 3 kg/cm$^2$ abs.

Examples of products of the invention are those obtained by reacting, according to the general method described, the listed pairs in the order fluoride-olefin:

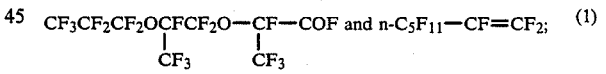 (1)

COF$_2$ and CF$_3$CF$_2$CF$_2$OCF=CF$_2$; (2)

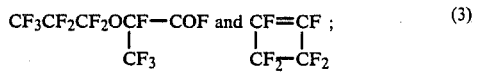 (3)

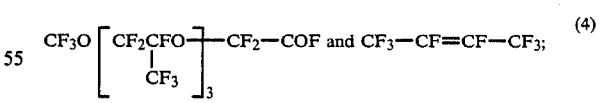 (4)

FOC—CF$_2$CF$_2$CF$_2$CF$_2$—COF and CF$_3$—O—CF=CF$_2$; (5)

FOC—CF$_2$OC$_2$F$_4$OCF$_2$—COF and C$_3$F$_6$; (6)

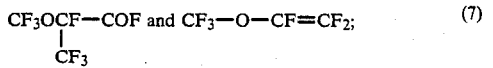 (7)

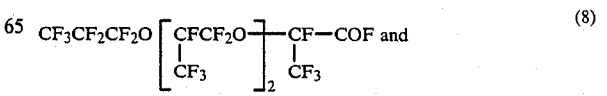 (8)

-continued $$CF_3CF_2CF_2CF_2CF_2—CF=CF_2;$$

$$CF_3CF_2CF_2O\left[\begin{array}{c}CF—CF_2O\\|\\CF_3\end{array}\right]_2 CF—COF \text{ and} \atop |\atop CF_3 \quad (9)$$

$$CF_3—CF_2CF_2CF=CF_2.$$

A further object of the present invention, which is apparent from the foregoing, is that of making available, by properly choosing the raw materials, a wide range of products which, though possessing all the properties which characterize the class of the invention, differ as regards the boiling point.

The combination of perfluoroether chain with oxetane rings leads therefore to very unexpected an unexpectable results, which render the compounds of the invention suitable for a plurality of uses.

The properties of the oxetane of the invention are all the more surprising as they are obtained also with side chains linked to the oxetane ring and containing only one ether oxygen atom.

The fluids according to this invention possess all the characteristics which render them suitable for being utilized in several industrial sectors, such as consistency with the materials, high dielectric strength, capability of evaporating without residues, low pour point, wide range between the boiling point and the pour point, non-flammability, non-explosivity and non-reactivity.

They can be used for the check tests of electronic devices, such as e.g. the thermal shock test, which consists in subjecting the electronic devices to sudden temperature changes in order to simulate extreme operative conditions. According to a present practice (US Mil Standard 883 B, 1011, 2), that is accomplished by alternately immersing the devices into two fluids maintained at very different temperatures (for example, $+150°$ C. and $-65°$ C.). The necessity of using two fluids depends on the fact that none of the fluids available on the market possesses such a wide range between boiling point and pour point.

With the oxetane of the present invention, conversely, it is possible to use one fluid only, which prevents a reciprocal pollution of the fluids and renders the test more rapid and less expensive, because all purification operations are abolished.

The fluids according to the present invention can be used, owing to their high dielectric strength ($\geq 40$ KV/2.54 mm at $20°$ C.) and volume resistivity ($\geq 10^{14}$ Ohm.cm at $25°$ C.) as well low dielectric constant ($\leq 2$ at $25°$ C.), for the cooling of electric devices under voltage without undergoing degradations and without causing circuit faults.

They are utilizable in the vapor phase soldering, for the soldering of surface mounted devices on printed circuits, and in the vapor phase curing for the curing of resins as they are stable over an indeterminate period of time at the boiling temperature in the presence both of metals and of the common materials utilized in these techniques; furthermore, as they consist of individual substances having a practically constant boiling point, they are not subject to losses due to preferential evaporation of the lower-boiling components, wherefore no variations occur in their composition.

Furthermore, they are utilizable in energy generation through Rankine organic cycles as they posses in addition to the already cited characteristics, a relatively high molecular weight, wherefore they require turbines with very small dimensions. A further applicative example of this kind is reported in R. E. Banks "Preparation, Properties and Industrial Applications of Organofluorine Compounds", Ellis Horwood, 1982.

The following examples are given to merely illustrate the invention, without being however a limitation thereof.

EXAMPLE 1

Into a photochemical unit consisting of a Hanau lamp TQ 150, with relevant quartz sheath and hollow space for the circulation of cooling water, and of a Pyrex glass reactor with an optical path of 0.5 cm thermoregulated at $-40°$ C. and with a coolant maintained at $-80°$ C., there were introduced 176 g (1.17 moles) of perfluoropropene and 125 g (0.25 moles) of the fluoride of the perfluoro-2,5-dimethyl-3,6-dioxanonanoic acid (obtained, according to conventional techniques, from the epoxide $C_3F_6O$ by oligomerization). The mixture was irradiated during 20 hours while stirring by means of a magnetic anchor. The rough reaction product was purified by fractionated distillation, removing, as head products, the unreacted components and leaving, as tails, 3 g of residue. There were collected 72 g of a colorless liquid, which was further purified by treatment with KOH tablets and by a re-distillation. The product distilled between $161°$ C. and $163°$ C. The IR spectrometric analysis of the product revealed the absence of reactive functional groups, in particular of carbonyl groups. The gaschromatographic analysis (GC) at $120°$ C. with 4 meter-columns of Fomblim/Chromosorb oils revealed individuals having retention times respectively of 9.29; 10.77; 12.00 minutes.

The NMR analysis $^{19}F$ carried out in bunching in a Varian apparatus with cryomagnet XL 200 revealed signals ($\delta$, ppm from $CCl_3F$) at:

range: 70–80 attributed to $—CF_3$ and $CF_2O—$;

128 attributed to $—CF_2\overline{CF}_2CF_3$ 144 attributed to $—OCF_2\overline{CF}OCF_2—$;
$\quad\quad\quad\quad\quad\quad\quad\quad\quad\quad\quad |$
$\quad\quad\quad\quad\quad\quad\quad\quad\quad\quad\quad CF_3$ range: 120–140 attributed to $—\overline{CF}O—$ (different from the one indicated at 144)

and

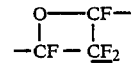

range: 175–185 attributed to O——CF—
$\quad\quad\quad\quad\quad\quad\quad\quad\quad\quad\quad\quad |\quad\quad |$
$\quad\quad\quad\quad\quad\quad\quad\quad\quad\quad\quad CF_2—\underline{CF}—CF_3$ On the basis of the analytical data, including the NMR integration, the synthesis product proved to be a 90:10 mixture of:

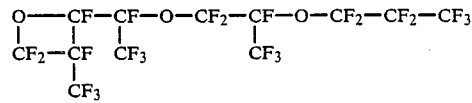

and

-continued $$O-CF-CF-O-CF_2-CF-O-CF_2-CF_2-CF_3$$
$$|\quad\quad|\quad\quad|\quad\quad\quad\quad|$$
$$CF-CF_2\ CF_3\quad\quad\quad CF_3$$
$$|$$
$$CF_3$$

and the cis, trans and optic isomers thereof.

The product obtained was characterized by:

| | |
|---|---|
| Boiling point (b.p.) (760 mm Hg) | 162° C. |
| vapor tension (20° C.) | 4 mm Hg |
| critical temperature | 278° C. |
| thermal conductivity (at 30° C.) | $157.10^{-6}$ cal/cm. sec., |
| surface tension (at 20° C.) | 19 dynes/cm |
| viscosity (at 20° C.) | 2.1 cSt |
| density (at 20° C.) | 1.805 g/ml. |
| dielectric strength | 48 KV/2.54 mm |

EXAMPLE 2

By operating with the same apparatus and according to the same modalities described in example 1, there were reacted 180 g (0.27 moles) of the fluoride of perfluoro-2,5,8-trimethyl-3,6,9-trioxadodecanoic acid (prepared as the corresponding compound of example 1) and 120 g (0.80 moles) of $C_3F_6$.

There were obtained 98 g of a colorless liquid having a b.p. of 201° C. at 760 mm Hg; on the basis of the analysis results, said liquid proved to be a mixture of the following compounds (in their isomeric forms):

$$O-CF-CF-(OCF_2CF)_2-O-CF_2-CF_2-CF_3$$
$$|\quad\quad|\quad\quad|\quad\quad\quad\quad|$$
$$CF_2-CF\ CF_3\quad\ CF_3$$
$$|$$
$$CF_3$$

$$O-CF-CF-(OCF_2CF)_2-O-CF_2-CF_2-CF_3,$$
$$|\quad\quad|\quad\quad|\quad\quad\quad\quad|$$
$$CF-CF_2\ CF_3\quad\ CF_3$$
$$|$$
$$CF_3$$

EXAMPLE 3

Using the same apparatus of example 1, there were reacted 48.3 g (0.146 moles) of the fluoride of perfluoro-2-methyl-3-oxahexanoic acid (prepared as described in example 1) and 175 g (0.5 moles) of perfluoro-heptene-1.

Photolysis was carried on until a gaschromatographic analysis of the reacting mixture revealed that the acid fluoride was present in an amount below 1%.

By rectification there were isolated 92.5 g of a colorless liquid having a b.p. of 175° C., which provided to be a mixture of the position isomers and of the optic isomers having the formula:

$$O-CF-CF-OCF_2CF_2CF_3$$
$$|\quad\quad|\quad\quad|$$
$$|\quad\quad|\quad CF_3$$
$$CF_2-CF-(CF_2)_4-CF_3$$

EXAMPLE 4

Following the modalities of example 1 there were reacted 164.1 g (0.617 moles) of $CF_3CF_2CF_2OCF=CF_2$ and 76.2 g (0.153 moles) of $$CF_3CF_2CF_2OCFCF_2OCFCOF$$
$$|\quad\quad\quad\quad\ |$$
$$CF_3\quad\quad\quad CF_3$$

The olefin employed has been obtained according to conventional techniques from the corresponding fluoride.

After a 38-hour photolysis and after fractionation, 95.3 g of a colorless liquid having a b.p. of 194° C. were obtained.

On NMR $^{19}$F analysis the same signals as noticed on the product of example 1 were observed, except the ones in the range 175-185 ppm, attributed to CF in position 3 in accordance with the fact that in this case it was adjacent to an oxygen atom and its signals fell within the range 120-140 ppm as for the —CF—O.

EXAMPLE 5

Following the same procedures described in example 1 there were reacted 124 g (0.19 moles) of the fluoride (prepared according to conventional techniques by fluorination of the corresponding acid) of the formula:

$$CF_3O\left[\begin{array}{c}CF_2CFO\\|\\CF_3\end{array}\right]_3 CF_2COF$$

and 200 g (1.33 moles) of $C_3F_6$. Photolysis was carried on till the fluoride content was reduced to less than 3%.

After purification, 132 g of a colorless liquid having a b.p. of 204° C. were isolated; such liquid, subjected to analysis, proved to consist of:

$$O-CF-CF_2O\left[\begin{array}{c}CFCF_2O\\|\\CF_3\end{array}\right]_3 CF_3$$
$$|\quad\quad|$$
$$CF_2-CFCF_3$$

and the corresponding isomers.

EXAMPLE 6

Employing the same procedures and the same apparatus described in example 1, there were reacted 222 g (0.84 moles) of
$CF_3CF_2CF_2OCF=CF_2$
and 90 g (0.22 moles) of $CF_3(CF_2)_6COF$, obtained by fluorination, according to known techniques, from the corresponding acid. After a 20-hour irradiation, the unreacted alkene and fluoride were removed by rectification and 80 g of oxetane having a b.p. of 189° C. were isolated.

The NMR $^{19}$F spectrum, analogously with what has been described in example 4, did not reveal signals in the range 175-185 ppm. The other signals were in accordance with the expected structure.

EXAMPLE 7

240 g (0.72 moles) of $$CF_3CF_2CF_2OCFCOF$$
$$|$$
$$CF_3$$

(prepared according to the technique of Ex. 1) and 350 g (2.33 moles) of $C_3F_6$ were introduced into a photochemical unit, similar to the one described in example 1, with the exception that stirring was secured by a membrane pump type N. 79 KW/18 manufactured by KMF, which conveyed $C_3F_6$, condensed by the cooler, to the reactor bottom.

After 40 hours there were isolated, by distillation in the range of 112°–113° C., 170 g of product which, as shown by the analyses, exhibited the expected structure.

EXAMPLE 8

According to the same procedures of example 1 and in a reactor analogous with the one therein described, but with an optical path of 0.1 cm, there were reacted 30 g (0.06 moles) of the fluoride of perfluoro-2,5-dimethyl-3,6-dioxanonanoic acid and 30 g (0.19 moles) of perfluorocyclobutene (prepared by dechlorination, according to conventional techniques, of 1,2-dichlorohexafluorcyclobutane).

It was irradiated during 8 hours and, after removal, by rectification of the unreacted acid fluoride and of the unreacted cycloolefin, 9.5 g of a fluid product were obtained, which, on the basis of the data obtained from NMR $^{19}F$, IR and GC analysis, proved to be the oxetane of the formula:

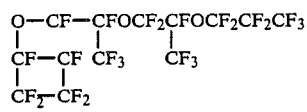

EXAMPLE 9

To evaluate the suitability of the oxetane of example 1 for being utilized at low temperatures, it was subjected to a differential thermal analysis in a Du Pont 900/951 apparatus at cooling ranges of 10°/min. till reaching a temperature of −140° C. No 1st order transition phenomena were observed; the 2nd order transition appeared at −118° C.

When carrying out the same determination on the product of example 2, 1st order transition phenomena were not observed, while the 2nd order transition appeared at −109° C.

Always to the same purpose, the pour point was determined, according to ASTM D 97/66, on the oxetane of example 1; such pour point proved to be −91° C.

EXAMPLE 9 (COMPARATIVE TEST)

The oxetane of the art, obtained from $CF_3(CF_2)_6COF$ and $C_3F_6$ according to the technique of example 1, was subjected to thermal-differential analysis. In this case, 1st order transition phenomena were observed at −50.5° C. and the pour point was higher than this temperature.

EXAMPLE 10

To evaluate the suitability of the oxetane of example 1 for being utilized at high temperatures, it was heated, by means of a thermostat, during 500 hours at 150° C. in the presence of steel AISI 316 and air, for the thermal shock test.

A comparison by means of IR spectrography, NMR $^{19}F$, GC between the sample so treated and the one not so treated did not reveal any differences.

EXAMPLE 11

To evaluate the thermal stability of the oxetane of example 1, 0.3 g of product were introduced into a spheric cell made of Hastelloy of an ARC calorimeter (Accelerating Rate Calorimeter); it was then heated in a nitrogen atmosphere, and no decomposition was observed up to 450° C.

By operating in the same apparatus, but in an air atmosphere, the thermo-oxidative stability was evaluated: the decomposition threshold was observed at 400° C.

EXAMPLE 12

To evaluate the consistency with plastomers and elastomers, there were immersed into the oxetane of example 2, maintained at 70° C., and kept therein during 72 hours, weighed test pieces, having sizes 4×0.5×0.2 cm, of the following polymers: polymethylmethacrylate, polyethylene ABS, PVC, polybutylene terephthalate, polystyrene, nylon-6, polycarbonate, polysulphone, ethylene-propylene-ethylidenenorbornene terpolymer, butadiene-acrylonitrile copolymer, the ethyl acrylate-butyl acrylate copolymer.

The test pieces, taken out from the bath, were carefully dried by means of filter paper and weighed again.

In no case were alterations in appearance observed, except for the last test piece, which appeared swollen. it exhibited a weight increase of 7.9%. In the case of the butadieneacrylonitrilene copolymer, a weight decrease of 0.4% was determined. In all the other cases, the weight variation was of the order of max.±0.2%.

What is claimed is:

1. Fluids having an oxetane structure, liquid up to a temperature of at least −70° C., having a boiling temperature of at least +50° C. and defined over a range of at maximum 4° C., and having a formula selected from amongst the following classes of compounds:

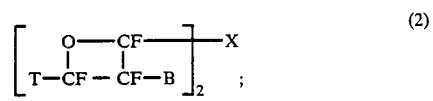

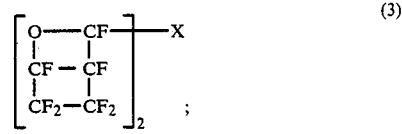

wherein A=F, or a perfluoroalkyl radical $R_f$ having 1 to 8 carbon atoms, or a group $OR_f$, or a group:

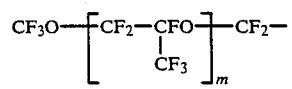

in which m is an integer from 0 to 5, or a group:

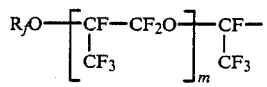

in which
$R_f$ and m have the same meanings as defined hereinabove;
B and T either like or unlike each other are:
F, a perfluoroalkyl radical with 1 to 7 carbon atoms, a group

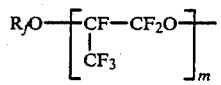

in which m and $R_f$ have the same meanings as defined hereinbefore, X is a group:

$-CF_2O(CF_2O)_p(C_2F_4O)_q-CF_2-$ in which p and q, either like or unlike each other, are integers from 0 to 5, and where the sum p+q is at least 1, or X is a group $-(CF_2)_r-$, in which r is an integer from 1 to 8; and being characterized in that at least one of the groups A, B, T in Class 1, or B and T in Class 2, or group A in Class 4, is different from fluorine and in that at least one of the groups A, B, T in Class 1, or B, T and X in Class 2, or X in Class 3, or A in class 4, contains one or more oxygen atoms;

and furthermore characterized in that when one of the radicals B or T is equal to the group:

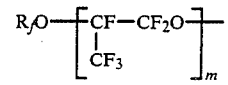

then the other is equal to F.

2. Fluids having an oxetane structure according to claim 1, of Class (1), in which $A=CF_3-CF_2-$, $CF_3(CF_2)_6-$, or

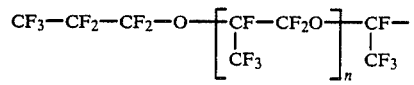

in which
n=0, 1, 2;
B and T, either like or unlike each other, are selected from:
$-F$, $-CF_3$, $CF_3(CF_2)_4-$, or one of B and T is

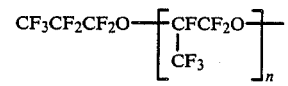

wherein n=0, 1, 2, the other being F.

* * * * *